(12) United States Patent
Marks et al.

(10) Patent No.: US 7,291,293 B2
(45) Date of Patent: Nov. 6, 2007

(54) VAPOR DEPOSITED ELECTRO-OPTIC FILMS SELF-ASSEMBLED THROUGH HYDROGEN BONDING

(75) Inventors: Tobin J. Marks, Evanston, IL (US);
Peiwang Zhu, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 10/789,928

(22) Filed: Feb. 27, 2004

(65) Prior Publication Data

US 2005/0127337 A1    Jun. 16, 2005

Related U.S. Application Data

(60) Provisional application No. 60/450,907, filed on Feb. 28, 2003.

(51) Int. Cl.
*F21V 90/00* (2006.01)
*G02F 1/35* (2006.01)

(52) U.S. Cl. .................. 252/586; 252/582; 359/245; 359/326; 359/328; 385/131; 385/143

(58) Field of Classification Search ............... 252/586
See application file for complete search history.

(56) References Cited

U.S. PATENT DOCUMENTS 3,947,410 A    3/1976   Meyer 4,410,563 A * 10/1983  Richter et al. .............. 427/108
6,855,274 B1 * 2/2005  Marks et al. ................ 252/582

FOREIGN PATENT DOCUMENTS

DE    3620825 A1    12/1987
GB    1398993       6/1975

OTHER PUBLICATIONS

Zhu, Peiwang; Kang, Hu; Facchetti, Antonio; Evmenenko, Guennadi; Dutta, Pulak; Marks, Tobin J. Vapor Phase Self-Assembly of Electrooptic Thin Films Via Triple Hydrogen Bonds. Department of Chemistry and Department of Physics as Astronom, Northwestern University, Evanston, Illinois 60208. JACS Communications, Published on Web Aug. 30, 2003; 11496 J. Am. Chem. Soc. 2003, 125, 11496-11497.

(Continued)

*Primary Examiner*—Randy Gulakowski
*Assistant Examiner*—Timothy J. Kugel
(74) *Attorney, Agent, or Firm*—Reinhart Boerner Van Deuren, S.C.

(57) ABSTRACT

The present invention introduces a novel route toward microstructural orientation into organic films, using multiple hydrogen-bonding to self-assemble chromophore molecules into electro-optic films in a net polar orientation. High-quality, thick films (up to micrometers) with molecular net dipole orientations can be fabricated under vacuum in hours. The film microstructure is intrinsically acentric; and the orientation is robust.

18 Claims, 7 Drawing Sheets

OTHER PUBLICATIONS

Zhu, Peiwang; Kang, Hu; Facchetti, Antonio; Evmenenko, Guennadi; Dutta, Pulak; Marks, Tobin J. Electro-Optic Thin Films Self-Assembled via Multiple Hydrogen Bonds From the Vapor Phase. Department of Chemistry and Materials Research Center, Northwestern University; 2145 Sheridan Road, Evanston, Illinois 60208. Department of Physics and Astronomy, Northwestern University, 2145 Sheridan Road, Evanston, Illinois 60208. Polymeric Materials: Science & Engineering 2003 89, 265.

Lin, Wenbin; Lin, Weiping; Wong, George K.; and Marks, Tobin J. Supramolecular approaches to second-order nonlinear optical materials. Self-assembly and microstructural characterization of intrinsically acentric [(Aminophenyl)azo]pyridinium superlattices. J. Am. Chem. Soc. 1996, 118, 8034-8042.

Cai, C.; Muller, B.; Weckesser, J.; Barth, J.V.; Tao, Y.; Bosch, M.M.; Kundig, A.; Bosshard, C.; Biaggio, I.; and Gunter, P. Model for in-plane directional ordering of organic thin films by oblique incidence oranic molecular beam deposition. Advanced Materials, Communications, Feb. 1999.

Cai, C.; Bosch, M.M.; Muller, B.; Tao, T.; Kundig, A.; Bosshard, C.; Gan, C.; Biaggio, I.; Liakatas, I.; Jager, M.; Schwer, H.; and Gunter, P. Oblique incidence organic molecular beam deposition and nonlinear optical properties of organic thin films with a stable in-plane directional order. Advanced Materials, Communications, Marc 1999.

Muller, B.; Cai, C.; Kundig, A.; Tao, Y.; Bosch, M.; Jager, M.; Bosshard, C.; and Gunter, P. In-plane alignment of noncentrosymmetric molecules by oblique-incidence molecular beam deposition. Applied Physics Letters, v. 74, May 21, 1999.

Muller, B.; Cai, C.; Bosch, M.; Jager, M.; Bosshard, C.; Gunter, P.; Barth, J.V.; Weckesser, J.; and Kern, K. ordering of PVBA on amorphous $SiO_2$ and Pd(110). Thin Solid Films, 343-344 (1999), 171-174.

Cai, C.; Bosch, M.M.; Tao, Y.; Muller, B.; Gan, Z.; Kundig, A.; Bosshard, C.; Liakatas, I.; Jager, M.; and Gunter, P. Self-assembly in ultrahigh vacuum: Growth of organic thin films with a stable in-plane directional order. J. Am. Chem. Soc. 1998, 120, 8563-8564.

Forrest, S.R.; Burrows, P.E.; Stroustrup, A.; Strickland, D.; and Ban, V.S. Intense second harmonic generation and long-range structural ordering in thin films of an organic salt grown by organic vapor phase deposition. Appl. Phys. Lett. 68 (10), Mar. 4, 1996.

\* cited by examiner

A (Prior art)

$X_2$ is the normal of the surface

B (Prior art)

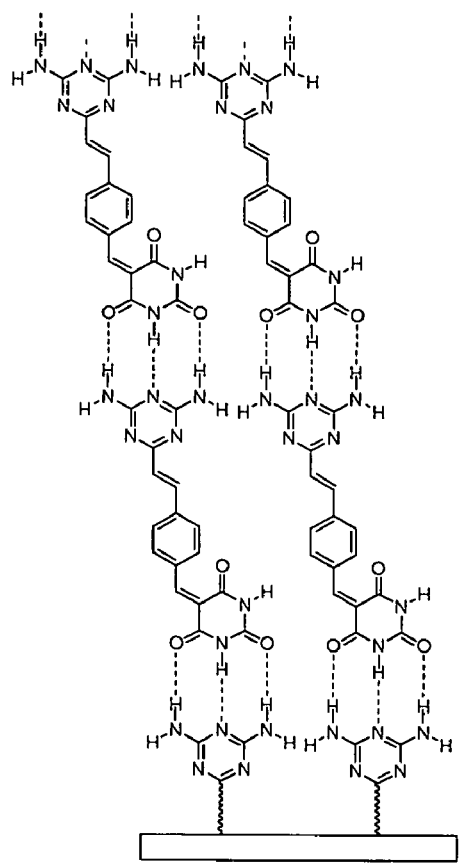
C
Fig. 1 con't.
Fig. 2
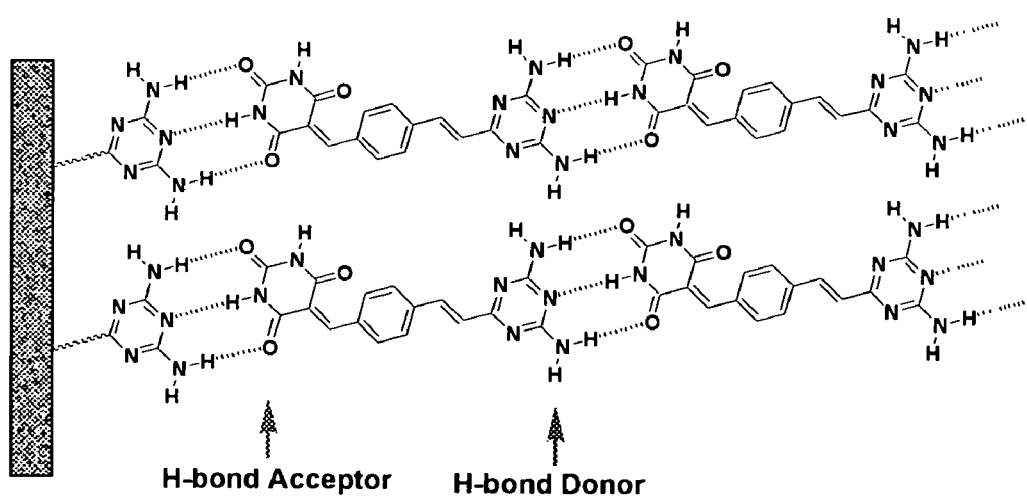

n = 0, 1, 2, ......

VAPOR DEPOSITED ELECTRO-OPTIC FILMS SELF-ASSEMBLED THROUGH HYDROGEN BONDING

This application claims priority benefit from prior U.S. provisional application Ser. No. 60/450,907, filed Feb. 28, 2003, the entirety of which is incorporated herein by reference.

The United States government has certain rights to this invention pursuant to Grant No. N000-14-00-C from the Office of Naval Research to Northwestern University.

BACKGROUND OF THE INVENTION

Molecule-based photonic materials represent a promising direction in the quest to develop novel electro-optic (EO) modulators promising greatly increased rates of information transmission by enhancing optical network speed, capacity, and bandwidth for data networking and telecommunications. Non-centrosymmetry is one of the basic requirements of these materials. Currently, three major methodologies are being used to achieve molecular orientation: electric-field (EF) poling, Langmuir-Blodgett (LB) film transfer, and layer-by-layer self-assembly (SA). In the first one, nonlinear optical (NLO)-active chromophores are either doped in or covalently bonded to a polymer to fabricate films. A high external electric field is then applied while the films are heated to around the glass transition temperature (Tg) to cause the chromophore dipoles to align in the direction of the electric field. It is a straightforward procedure to fabricate thick-poled films. However, the drawbacks are: 1) the orientation achieved by EF-poling is not indefinitely stable after removal of the EF; 2) due to strong dipole-dipole interactions among the chromophore molecules, the doping concentration cannot be brought to a high level; 3) microdomains formed during EF-poling can increase the optical loss in a waveguide device.

For the LB film approach, only limited chromophores with long alkyl groups can be used. Since weak van der Waals interactions are the main structural driving force, the orientation becomes progressively worse as the film becomes thicker (e.g., after 100 layers). Other drawbacks include low NLO response and poor mechanical strength. For covalent self-assembly, the NLO response is strong, orientation is stable, and film quality is good. However, the main disadvantage is the time-consuming nature of the fabrication procedure (hundreds of hours might be used to achieve a micrometer thickness film). Additional synthetic complexity arises from use of moisture-sensitive reagents.

Although H-bonds are widely used in crystal engineering, the prior art is not directed to thin film deposition using H-bonding constituents. Since thin acentric films are needed for EO modulators, efficient new depositions methods would be of great utility. Dipolar orientations driven by H-bonds have been reported in drop-cast films. However, the H-bonding modules come from two different compounds (FIG. 1, structure A), and the films obtained are composites, and not derived from the vapor phase. A technique known as "oblique incidence organic molecular beam deposition" was also reported to produce oriented films with single H-bonds used to align chromophore molecules (FIG. 1, Structure B). However, the molecular dipoles are parallel to the substrate. Only in-plane directional ordering is achieved (FIG. 1, structure B). As is well known, in a waveguiding EO modulator device, the molecular dipoles must be oriented perpendicular to the substrate plane so that maximum EO coefficient, $r_{33}$, can be achieved.

Vapor deposition techniques have previously been used in the art to fabricate ordered NLO organic films, such as stilbazolium salts, polydiacetylenes, etc; however, the driving forces do not involve H-bond formation. In stilbazolium salt films, the chromophore is generated in situ, and in ordered polydiacetylene films, van der Waals interactions play important roles. Reaction considerations limit the former, while unstable structural orientations plague the latter. As a result, the art continues its search for a facile assembly of robust films of NLO-active chromophores.

BRIEF DESCRIPTION OF THE DRAWINGS

FIG. 2. A schematic representation illustrating orientation of a chromophore of this invention, on a substrate.

With reference to FIG. 8, molecular structures of several general NLO-active core components of chromophores, in accordance with this invention, where $R_1$—$R_3$ are independently selected from H, alkyl, electron-donating substituents or electron withdrawing substituents, and m and n are integers described elsewhere herein.

With reference to FIG. 8, molecular structures of several D (FIG. 10A) and A (FIG. 10B) moieties/modules. 10A: $R_1$ and $R_2$ are independently selected from H, alkyl or other electron-donating or withdrawing substituent groups. One of the substitutents groups $R_3$, $R_4$, and $R_5$, is $Ar^1$. 10B: one of the substitutents $R_6$, $R_7$, and $R_8$ is $Ar^2$; X may be O or S.

SUMMARY OF THE INVENTION

In light of the foregoing, it is an object of the present invention to provide acentric electro-optic films and/or compounds, compositions, composites and/or methods for their production and/or assembly, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide a molecular-based electro-optic film with a stable, microstructural polar orientation without resort to time-consuming fabrication procedures of the prior art.

It is another object of this invention to provide one or more class of compounds for use in the self-assembly of multi-layered compositions, as can be used in the preparation of a range of electro-optic films, composites and/or modulator devices.

Other objects, features, benefits and advantages of the present invention will be apparent from this summary and its descriptions of various embodiments and will be readily apparent to those skilled in the art having knowledge of various electro-optic films, modulators, related devices and associated assembly/production techniques. Other objects, features, benefits and advantages will be apparent from the above as taken into conjunction with the accompanying examples, data, figures and all reasonable inferences to be drawn therefrom.

Figure 1:
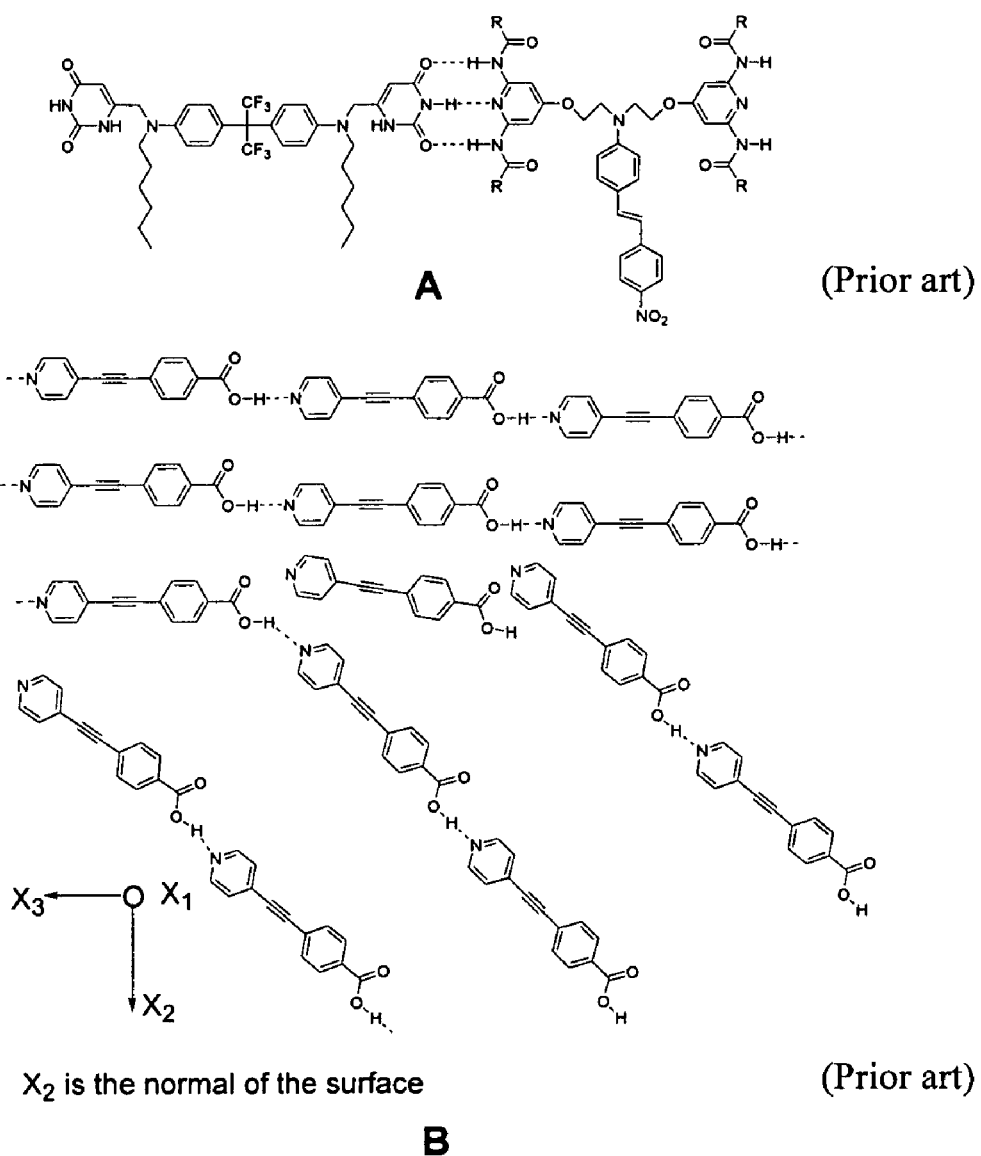
FIG. 1. Prior art structures A and B, in comparison with structure C, as represented illustrating multiple H-bonds between 5-{4-[2-(4,6-diamino-[1,3,5]triazin-2-yl)-vinyl]-benzylidene}-pyrimidine-2,4,6-trione (DTPT) molecules, in accordance with this invention.

The present invention relates to the use of multiple hydrogen-bond donors and acceptors in an NLO active chromophore molecular core. Specifically designed intermolecular H-bonds provide chromophore alignment in the desired direction (head-tail and perpendicular to the substrate plane) from vapor phase to form solid films (FIG. 1, structure C). Out-plane non-centrosymmetric microstructures are achieved in the deposited films, and this acentricity is intrinsic. H-bonding, stronger than van der Waals forces, provides a dipole orientation stable with time, and results in good film mechanical strength. The chromophores are not moisture-sensitive, and the films are convenient to handle. Vapor deposition techniques can be adopted to fabricate films. The process is rapid using available synthetic techniques (micrometer thick films can be deposited in hours), and the film surface is quite smooth (the root-mean-square, rms, roughness is only a few nanometers for a micrometer thick film). This invention provides the first use of a plurality of H-bonds as a driving force and/or enroute to the preparation of microstructurally acentric (with the net dipolar orientation perpendicular to the substrate surface) self-assembled films from the vapor phase.

With reference to the preceding, the present invention comprises compounds which can be represented by a formula

Figure 8:
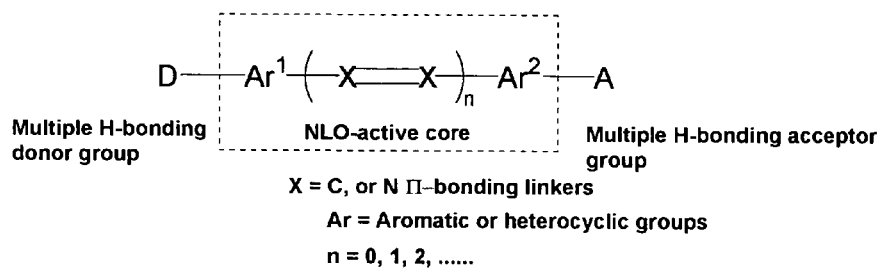
FIG. 8. A schematic formula, in accordance with certain embodiments of this invention.
Figure 9:
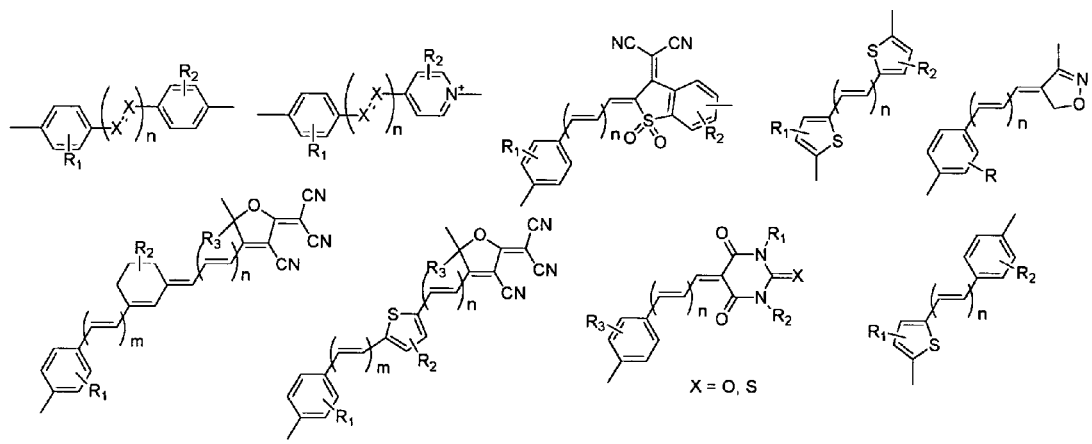
FIG. 9.

$$D—Ar^1_x—(X=X)_n—Ar^2_y—A \quad (1)$$

wherein D is a moiety with a plurality of functional groups capable of hydrogen donation; $Ar^1$ and $Ar^2$ are aromatic or heterocyclic moieties; X is carbon or a heteroatom component providing π-bonding capability; n is an integer greater than or equal to 0; x and y are independently integers greater than 0, providing their sum is at least 1; and A is a moiety with a plurality of functional groups capable of hydrogen-acceptance in the formation of a hydrogen bond. With reference to the compounds of formula 1, the Ar and X components can be considered as comprising a core chromophore molecular structure, as discussed elsewhere herein, in the context of an NLO material. Without limitation reference is made to FIGS. 8 and 9, the latter of which provides a number of such core molecular structures. As illustrated by FIG. 9, $Ar^1$ and $Ar^2$ can be but are not limited to phenyl, naphthyl, pyridine, pyrimidine and thiophene and other aromatic, polycyclic and heterocyclic moieties, wherein $R_1$, $R_2$ and $R_3$, etc. can be hydrogen or a substituent provided for desired structural or electronic (e.g., electron-donating or electron-withdrawing, as would be understood by those in the art) effect. Likewise, with reference to FIG. 9, it will be understood by those skilled in the art that a plurality of such aromatic or heterocyclic moieties can be structurally coupled to one or more π-bonding components with a corresponding number of single- or multiple-bond components, whether or not conjugated with $Ar^1$ and/or $Ar^2$. Such NLO-active core structures can vary or be designed to optimize nonlinearity, working wavelength, stability and associated electro-optic properties.

Figure 10A:
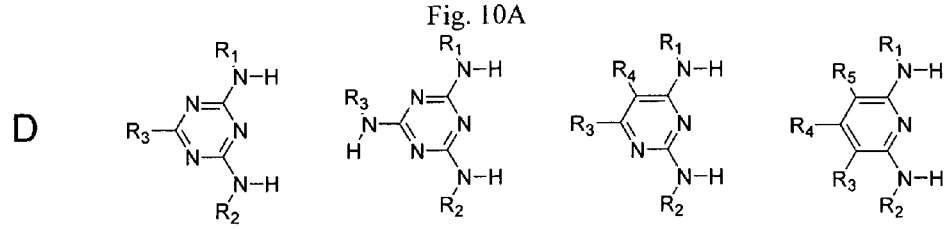
FIGS. 10A-10B.
Figure 10A:
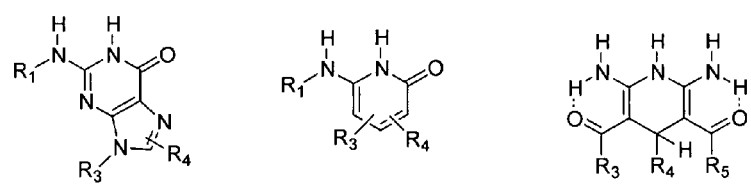
Figure 10B:
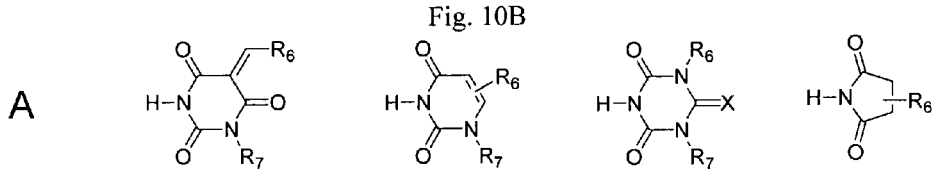
Figure 10B:
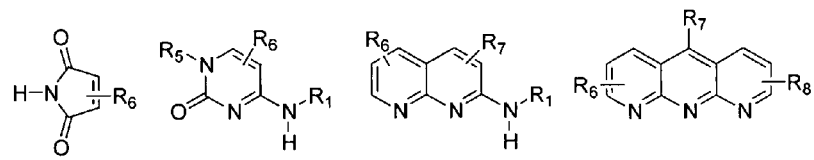

Without limitation, representative hydrogen-donor (D) and acceptor (A) moieties are shown, respectively, in FIGS. 10A-10B. Compounds 1, above, can be prepared incorporating such and other donor and acceptor moieties using well-known synthetic precursors and prepatory techniques, including but not limited to the coupling or condensation reactions and related procedures illustrated in Scheme 1, such procedures as can be varied without undue experimentation by choice of hydrogen donor, acceptor carbon/heteroatom component and aromatic heterocyclic moiety precursors, appropriately substituted for such reaction, en route to a particular compound of formula 1.

With reference to the preceding discussion of compounds 1, structural modules/components/moieties and variations thereof and related precursors and synthetic techniques, the present invention can also be extended to include compounds 2-4, as can be represented by the respective structural formulae:

$$D—Ar^1—(X=X)_n—Ar^2—A \quad (2)$$

$$D—Ar^1—(X=X)_n—A \quad (3)$$

$$D—(X=X)_n—Ar^2—A \quad (4)$$

Depending upon the particular chromophore, single $Ar^1$ or $Ar^2$ moieties can be used in conjunction with a molecularly non-elongated (e.g., n=1) π-bonded component.

In part, the present invention can also include a method of using hydrogen-bonding for acentric chromophore molecular alignment perpendicular to a substrate plane. Such a method includes (1) providing a dipolar chromophore molecular component having a first terminal moiety with a plurality of functional groups capable of hydrogen donation, and a second terminal moiety with a plurality of functional groups capable of hydrogen acceptance; (2) contacting a substrate with such a chromophore molecular component, the substrate functionalized for hydrogen-bonding (e.g., for hydrogen donation or hydrogen acceptance) with the molecular component; and (3) contacting the molecular component with another such dipolar chromophore molecular component. In various embodiments, the chromophore components have acentric molecular structures, assembly of which in accordance with the present methodologies can provide corresponding multi-layered acentric films or coatings having a net dipolar orientation perpendicular to the plane of an associated substrate.

Molecular components useful with such a method include but are not limited the compounds of formulae 1-4, above. Identity of the terminal hydrogen donor and acceptor moieties are a matter of choice depending upon the degree of required hydrogen-bonding and desired chromophore core structures. As discussed elsewhere herein, such compounds and related methodologies can be utilized in the fabrication of a wide range of second-order NLO devices and associated multi-layered compositions and composites where smooth, transparent acentric films are required. Applications include but are not limited to electro-optic modulators, devices for doubling the frequency of lights and second harmonic generation.

EXAMPLES OF THE INVENTION

The following non-limiting examples and data illustrate various aspects and features relating to the compounds, composites and/or methods of the present invention, including the self-assembly of intrinsically acentric electro-optic media, as are available through the synthetic methodologies described herein. In comparison with prior art, the present methods and compounds/composites provide results and data which are surprising, unexpected and contrary thereto. While the utility of this invention is illustrated through the use of several compounds/composites and synthetic methods which can be used in conjunction therewith, it will be understood by those skilled in the art that comparable results are obtainable with various other compounds/compositions and associated methods, as are commensurate with the scope of this invention.

Materials and methods. Unless stated otherwise, chemicals were purchased from Aldrich Chemical Co. and used as received. Single-crystal silicon (100) substrates were purchased from Semiconductor Processing Company, Inc. NMR spectra were recorded on a VARIAN Mercury-400 MHz or VARIAN INOVA-500 MHz spectrometer. Mass spectra were recorded with a MICROMASS Quattro II Triple Quadrupole HPLC/MS/MS Mass Spectrometer. Elemental analyses were performed by Midwest Microlabs. UV-vis spectra were recorded on a Cary 1E spectrophotometer. Polarized second harmonic generation measurements were carried in the transmission mode with a Q-switched Nd:YAG laser operating at 1064 nm, with a pulse width of 3 ns at a frequency of 10 Hz. Atomic force microscopic images were recorded with a Nanoscope II instrument (Digital Instruments, Inc.).

Example 1

Illustrating one aspect of this invention is the design of a class of NLO-active chromophores containing multiple H-bond donors and acceptors: for example, 5-{4-[2-(4,6-diamino-[1,3,5]triazin-2-yl)-vinyl]-benzylidene}-pyrimidine-2,4,6-trione (DTPT, shown below). In this chromophore molecule, pyrimidine-2,4,6-trione and 4,6-diamino-1,3,5,-triazine moieties can form triple H-bonds between two neighboring molecules (FIG. 2). A head-tail structural configuration is provided by choice and design of the donor and acceptor moieties.

Example 2a

Figure 12:
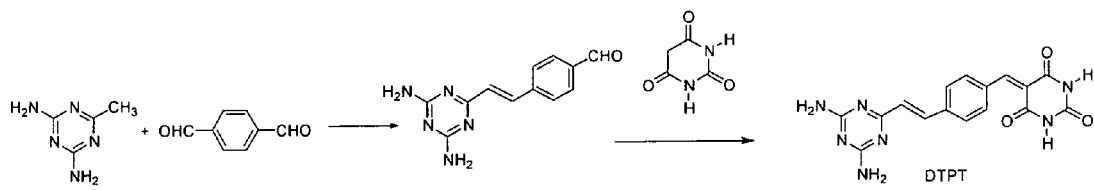
FIG. 12. Schematic illustration of the synthesis of 5-{4-[2-(4,6-diamino-[1,3,5]triazin-2-yl)-vinyl]-benzylidene}-pyrimidine-2,4,6-trione, a chromophore of this invention.

Synthetic Procedures. With reference to examples 2(b-c) below, one chromophore of this invention can be prepared according to the synthetic route illustrated in FIG. 12. This generally synthetic procedure and modifications thereof, as would be understood by those in the art, can be used en route to a range of acentric chromophore compounds, in accordance with this invention, such compounds as can vary depending upon choice of the aforementioned D, A, $Ar^1$, $Ar^2$ and π-bonding moieties or components.

Example 2b

Synthesis of 4-[2-(4,6-diamino-[1,3,5]triazin-2-yl)-vinyl]-benzaldehyde. To 107.2 g (800 mmol) of benzene-1,4-dicarboxaldehyde suspended in 450 mL methanol was added with stirring 294.0 g of 31% aqueous sulfuric acid (50 mL of concentrated sulfuric acid was added slowly to 200 mL of water while stirring). The solid dissolved and a yellow solution was obtained. The solution was heated to 80° C. with an oil bath, and 25.0 g (200 mmol) 6-methyl-[1,3,5]triazine-2,4-diamine powder was added. The solution was stirred at 80° C. for 8 h then cooled to room temperature. Next, 1.2 g of yellow byproduct (1,4-bis[4-[2-(4,6-diamino-[1,3,5]triazin-2-yl)-vinyl]]-benzene) was removed by filtration, and the filtrate was treated with 2000 mL water. The resulting solid was collected by filtration and washed with saturated aqueous $NaHCO_3$ and water until neutral. The excess benzene-1,4-dicarboxaldehyde was removed by sonicating and washing with acetone three times. Yield: 20.0 g of light yellow product. Yield=41%. $^1$HNMR (500 MHz, DMSO): δ9.992 (s, 1H), 7.894 (d, J=8.0 Hz, 2H), 7.847 (d, J=7.5 Hz, 2H), 7.806 (d, J=15.5 Hz, 1H), 6.928 (d, J=15.5 Hz, 1H), 6.806 (br, 4H). $^{13}$CNMR (500 MHz, DMSO): δ 193.914, 193.417, 170.671, 167.847, 141.836, 136.833, 131.461, 130.688, 128.883.

Example 2c

Synthesis of 5-{4-[2-(4,6-Diamino-[1,3,5]triazin-2-yl)-vinyl]-benzylidene}-pyrimidine-2,4,6-trione (DTPT). To 7.29 g (30 mmol) of 4-[2-(4,6-diamino-[1,3,5]triazin-2-yl)-vinyl]-benzaldehyde suspended in 150 mL of 1-pentanol at 130° C. was cautiously added 75 mL of hot aqueous sulfuric acid (25 mL of concentrated sulfuric acid was added to 50 mL of water with cautious while stirring). The solid dissolved immediately, and a yellow solution was obtained. To this solution, 4.61 g (36 mmol) of powdered barbituric acid was added while stirring vigorously at 140° C. Yellow precipitate appeared immediately. The mixture was slightly refluxed at 140° C. for 10 min then filtrated while it was hot. Solid washed with 50 mL of warm 1-pentanol, then suspended in 300 mL of water and neutralized with saturated aqueous $NaHCO_3$. The solid was collected by filtration and washed with water. Yield: 9.72 g of yellow product. Yield=88%. $^1$HNMR (400 MHz, DMSO): δ11.519 (s, 1H), 11.375 (s, 1H), 8.378 (s, 1H), 8.234 (d, J=8.0 Hz, 2H), 7.915 (d, J=16.0 Hz, 1H), 7.857 (d, J=8.0 Hz, 2H), 7.101 (br, 4H), 7.047 (d, J=16.0 Hz, 1H). m.p.>350° C. EA found: C, 52.20; H, 3.86; N, 26.12. Calculated for $C_{16}H_{13}N_7O_3 \cdot H_2O$: C, 52.03; H, 4.09; N, 26.55. MS (rel. abundance): $M^++1$ (68), $M++2$ (13), 242.1 (5), 217.1 (6), 179.0 (15), 157.0 (30), 101.0 (55), 79.1 (100). MS (high resolution, $ES^+$): $MH^+$ (352.1158).

Example 3a

Figure 13:
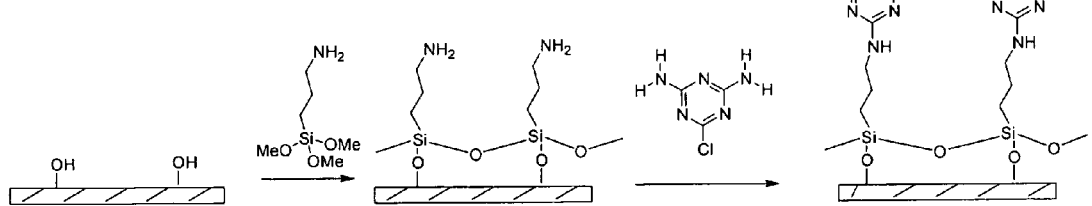
FIG. 13. Schematic illustration showing a general methodology for substrate functionalization and chromophore assembly.

Substrate Preparation and Functionalization. With reference to examples 3b-3d, a melamine template was anchored on substrates according to FIG. 13, illustrating a general methodology for substrate functionalization.

Example 3b

Cleaning of substrates. Sodium lime glass, fused quartz, and silicon wafer substrates were cleaned by immersion in "piranha" solution ($H_2SO_4$/30% $H_2O_2$ 7:3 (v/v)) (Caution: "Piranha" is an extremely dangerous oxidizing agent and should be handled with care using appropriate shielding) at 80° C. for 1 h. After cooling to room temperature, they were rinsed with deionized water and then subjected to an RCA-type cleaning protocol ($NH_3 \cdot H_2O$/$H_2O$/30% $H_2O_2$ 1:5:1 (v/v) at room temperature, 40 min). They were then washed with deionized water and dried in oven at 125° C. overnight. ITO glass substrates, as illustrated above, were first sonicated in aqueous detergent for 30 mins, then rinsed with deionized water. They were then sonicated in methanol, iso-propanol, and acetone for 30 min, respectively, and then dried in oven at 125° C. overnight. Other substrates suitable for use in conjunction with the present invention are provided in the U.S. Pat. No. 5,834,100, the entirety of which is incorporated herein by reference, such substrates as can be modified/functionalized as illustrated herein.

Example 3c

Self-Assembly of 3-aminopropyltrimethoxysilane. Substrates were loaded in an air-free reactor. The air inside of the reactor was replaced by dry $N_2$ using a Schlenk line. Then, 210 mL of 5% (v/v) 3-aminopropyltrimethoxysilane as a dry THF solution was transferred to the reactor. The solution was heated at 60° C. for 24 h. After that, the substrates were rinsed three times with THF. Alternatively, room temperature solution of 196 mL of 95% ethanol and 4 mL of 3-aminopropyltrimethoxysilane was allowed to stand for 10 min to ensure silanol formation. The substrates were then immersed in this solution for 10 min. They were next rinsed three times with 95% ethanol and dried in a dry $N_2$ stream, and cured for 10 min in a vacuum oven at 110° C.

Example 3d

Surface functionalization with 6-chloro-1,3,5-triazine-2, 4-diamine. A solution was prepared from 1.46 g (8.14 mmol) of 6-chloro-1,3,5-triazine-2,4-diamine and 0.410 g (5.00 mmol) NaOAc in 200 mL DMSO. The substrates were immersed in the solution for 24 h at room temperature. They were then washed with DMSO, water, and then acetone. Alternatively, the reagent (0.15 g) was suspended in 50 mL of 1-pentanol at 150° C. The 3-aminopropyltrimethoxysilane functionalized substrates were then loaded into the reactor. After refluxing for 24 h, they were cooled to room temperature and rinsed with 1-pentanol, deionized water, and acetone. Functionalization with a suitable hydrogen acceptor can be provided as would be understood by those in the art aware of this invention.

Example 4a

Sublimation of DTPT. To achieve further purification and to ascertain that DTPT (example 2c) is stable under sublimation conditions, the chromophore was gradient sublimed at 330° C./~3×10$^{-8}$ Torr for 24 h. The $^1$H NMR spectrum of the sublimed material is identical to that prior to sublimation. EA found: C, 54.21; H, 3.61; N, 26.60. Calculated for $C_{16}H_{13}N_7O_3$: C, 54.70; H, 3.73; N, 27.91. This result shows that the water of crystallization is lost on sublimation.

Example 4b

Figure 11:
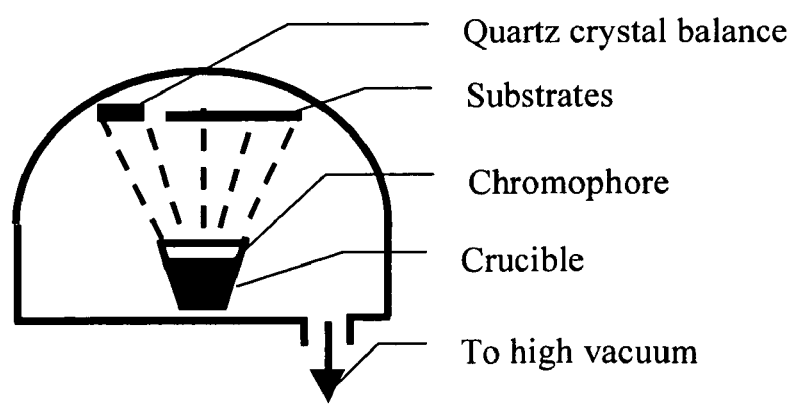
FIG. 11. Schematic illustration of an apparatus configuration for vapor deposition and growth of a chromophore film of this invention.

Film Deposition. FIG. 11 depicts an apparatus configuration, of the sort commercially available, which can be used to vapor deposit and grow the chromophore films of this invention. Vacuum pressures can typically range from about $10^{-5}$~$10^{-6}$ Torr, with a substrate temperature depending upon choice of chromophore and substrate. A calibrated quartz crystal balance was used to monitor the film growth rate and thickness. More specifically, a DENTON Vacuum DV-502 deposition apparatus ($10^{-5}$-$10^{-6}$ Torr) was then used to fabricate DTPT films at an optimized substrate temperature of 100° C. and growth rate of 0.5-2.0 Å/s which was controlled by adjusting the heating current of the crucible. The resulting film was optically transparent ($\alpha \approx 10$ cm$^{-1}$ at 640-1800 nm, $\lambda_{max}$=332 nm) and smooth by contact mode AFM (see Example 8, below). Deposit parameters and growth conditions will vary depending upon choice of chromophore, as will be understood by those skilled in the art made aware of this invention.

Example 5

Figure 3:
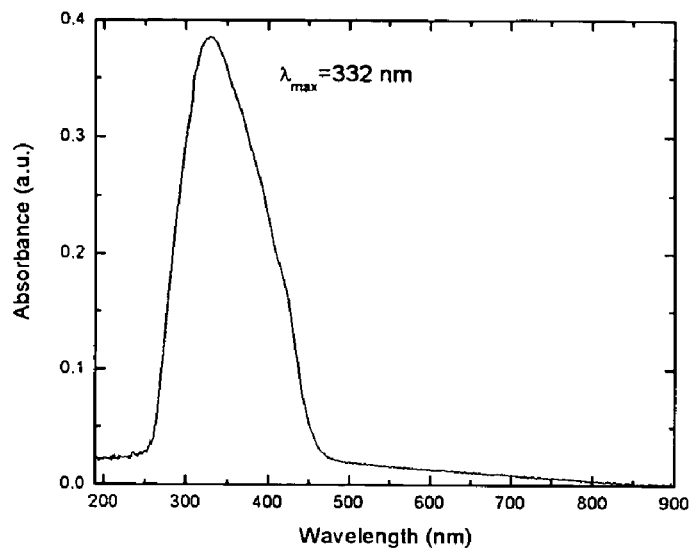
FIG. 3. UV-vis spectrum of vapor deposited DTPT film on quartz.

Optical UV-Vis Spectroscopy. Homogeneous substrate coverage deepening of the yellow color of the films deposited on transparent substrates can be clearly observed by eye. The film UV-vis spectrum shows an absorption peak around 332 nm (FIG. 3), which is slight blue shifted compared to the spectrum in DMSO solution.

Example 6

Figure 4:
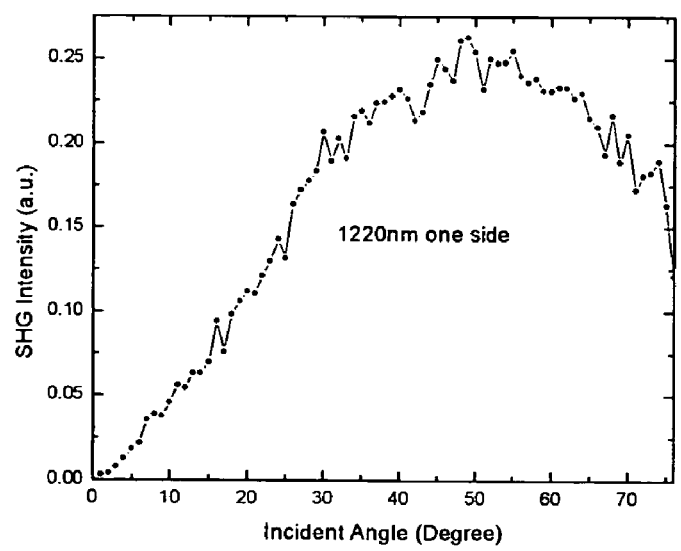
FIG. 4. Second harmonic generation (SHG) response as a function of fundamental beam incident angle from a float glass slide having a 1220 nm thick DTPT film on one side.
Figure 5:
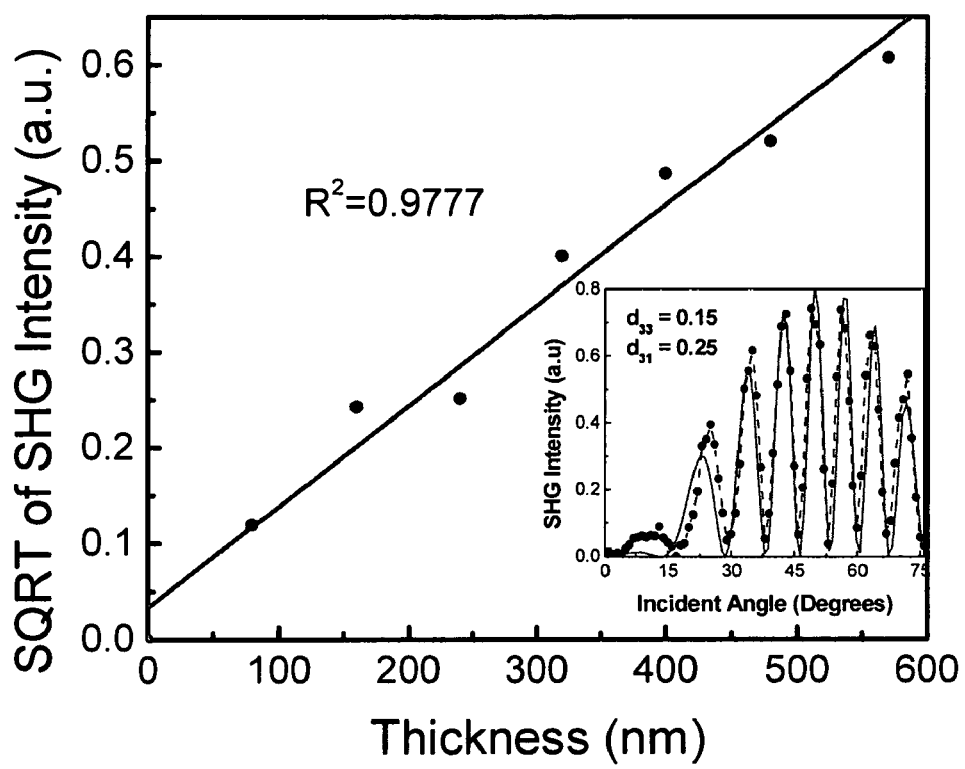
FIG. 5. Square root of second harmonic generation (SHG) response of DTPT films as a function of the thickness; Inset: SHG response as a function of fundamental beam incident angle from a float glass slide having DTPT films at the indicated thickness on both sides. The dashed line is drawn as a guide to the eye. The solid line is fitting result.

Second Harmonic Generation Experiments. Polarized transmission SHG measurements on the films at $\lambda_o$=1064 nm were carried out on samples placed on a computer-controlled rotation stage, enabling the incidence angle of the input radiation to the sample surface normal to be varied from 0° to 76°. For a sample with a film deposited on only one side, it shows the strongest SHG response at the incident angle about 50° (FIG. 4). Angle-dependent SHG interference patterns for glass substrates coated on both sides demonstrate that identical film quality and uniformity on both sides of the substrate have been achieved. A quadratic dependence of the 532 nm light output intensity ($I_{obs}^{2\omega}$) on the thickness of the DTPT film (FIG. 5) further demonstrates the uniformity of the chromophore orientation, and that the response is likely due to a bulk rather than interface effect. Calibrating the data in FIG. 5 with quartz crystal SHG intensity gives a $d_{33}$ of 0.15 pm/V and $d_{31}$ of 0.25 pm/V, values consistent with the modest computed molecular hyperpolarizability [$\beta_{tot}(\omega$=0.0 eV)=81×10$^{-30}$ esu for a linear trimer]. Using standard assumptions, the SHG analysis yields an average chromophore tilt angle of ~56.7° with respect to the substrate normal.

Example 7

Figure 6:
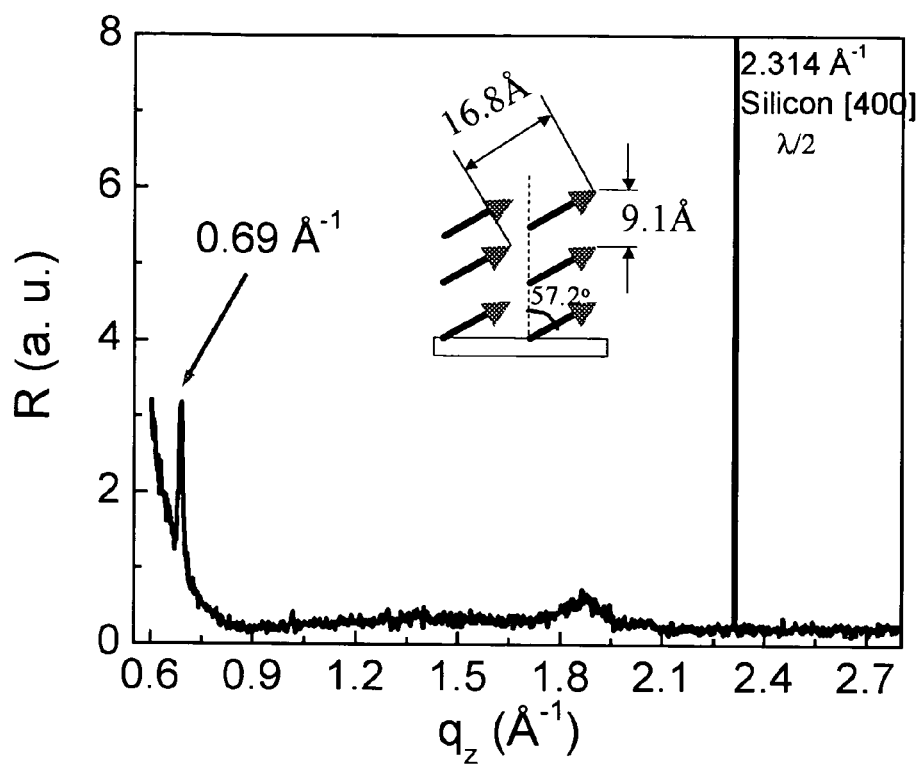
FIG. 6. X-ray diffraction pattern of a DTPT film grown on a functionalized Si (100) substrate; Inset: Proposed molecular alignment in film.

X-ray Diffraction. Synchrotron X-ray diffraction (XRD) was employed to probe microstructural similarity and determine the degree to which the non-centrosymmetric crystal structure of DTPT was achieved. In FIG. 6, a specular peak appears at 0.69 Å$^{-1}$, which corresponds to a layer-by-layer structure with a repeat distance of 9.1 Å. AM1-level molecular modeling shows the distance between DTPT molecules in a H-bonded chain is ~16.8 Å, which, combined with the XRD data yields a molecular tilt angle from the substrate normal of 57.20 in the films. (See, FIG. 6 inset and the schematic representation of FIG. 2.) This result is in good agreement with the SHG data of the preceding example and clearly shows out-plane ordering of chromophore molecules has been achieved and yields a similar tilt angle.

Example 8

Figure 7:
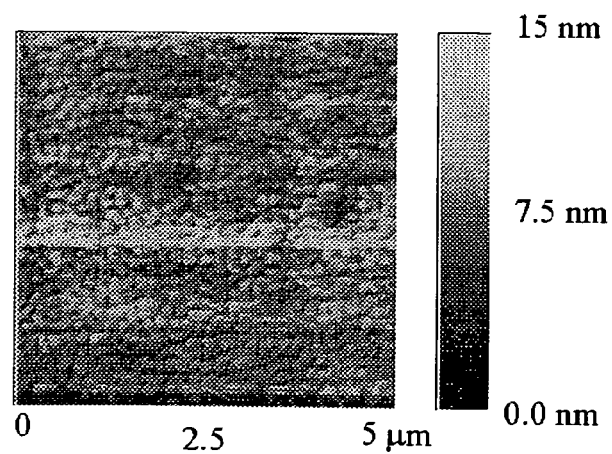
FIG. 7. Atomic Force Microscopy (AFM) image at 5×5 μm scan area of a DTPT film.

Atomic Force Microscopy. Contact mode AFM measurements on a 1.22 μm thick film sample reveal a smooth, high quality film. With a 5.0×5.0 μm scan area, the rms roughness is only 1.7 nm (FIG. 7).

As shown above, illustrating broader aspects of this invention, a donor-acceptor π electron chromophore was designed and synthesized. Multiple H-bonding interactions direct self-assembled chromophore alignment in the desired molecular head-to-tail direction using a straightforward vapor phase deposition process. Angle-dependent SHG interference patterns for glass substrates coated on both sides and the quadratic dependence of the 2ω light output intensity on chromophore film thickness demonstrate high, uniform film quality and polarity. XRD also demonstrates long-range, acentric microstructural order and yields a molecular tilt angle in good agreement with polarized SHG data, demonstrating out-of-plane ordering of chromophore alignment, of the sort useful in the context of electro-optic films and related devices.

We claim:

1. An intrinsically acentric chromophore compound of a formula

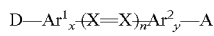

wherein D is a moiety comprising a plurality of hydrogen bond-forming hydrogen donor groups; A is a moiety comprising a plurality of hydrogen bond-forming hydrogen acceptor groups; (—X=X—) is a π-bonded component comprising at least one of carbon and a heteroatom; n, x and y are independently $\geq 0$; and x+y is $\geq 1$.

2. The chromophore compound of claim 1 wherein said $Ar^1$ and said $Ar^2$ are independently selected from phenyl, benzylidene, pyridinyl, pyrimidinyl, thiophenyl and thiazinyl moieties.

3. The chromophore compound of claim 2 wherein x+y=1.

4. The chromophore compound of claim 1 of a formula D—$Ar^1$—(X=X—)$_n$—$Ar^2$—A.

5. A chromophore compound of claim 1 of a formula D—$Ar^1$—(X=X—)$_n$—A.

6. The chromophone compound of claim 1 of a formula D—(X=X—)$_n$—$Ar^2$—A.

7. The chromophone compound of claim 1 wherein said D comprises a moiety having a structural formula selected from

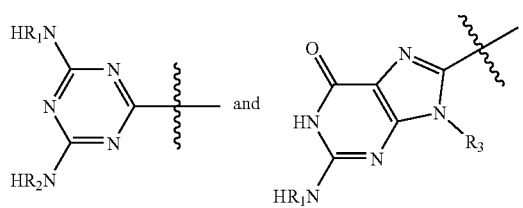

wherein $R_1$-$R_3$ are independently selected from hydrogen, electron-donating substituents and electron-withdrawing substituents.

8. The chromophore compound of claim 1 wherein said A comprises a moiety having a structural formula selected from

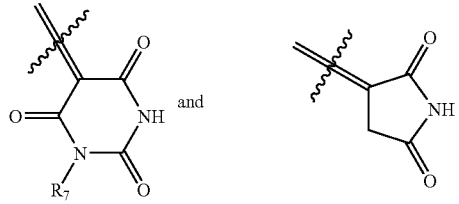

wherein $R_7$ is selected from hydrogen, electron-donating substituents and electron-withdrawing substituents.

9. The chromophore compound of claim 1 wherein (—X=X—)$_n$ comprises a moiety having a structural formula selected from (—C=C—)$_n$ and

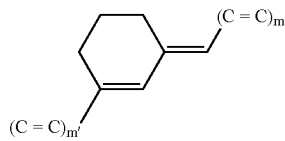

wherein m+m'$\geq$1.

10. An intrinsically acentric chromophore compound of a formula

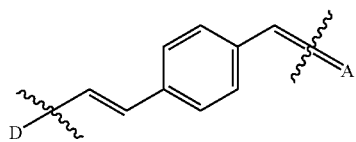

wherein D is a moiety having a structural formula selected from

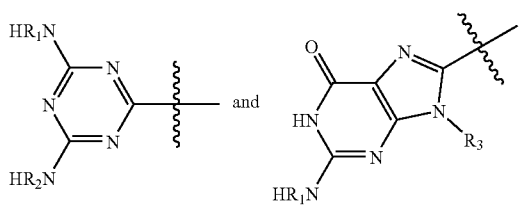

and A is a moiety having a structural formula selected from

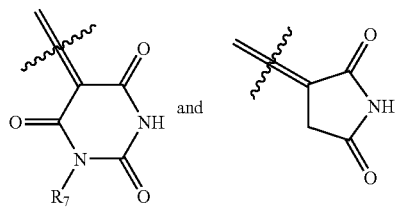

wherein $R_1$, $R_2$, $R_3$ and $R_7$ are independently selected from hydrogen, electron-donating substituents and electron-withdrawing substituents.

11. The chromophore compound of claim 10 wherein said D comprises a triazin-2-yl moiety of a structural formula

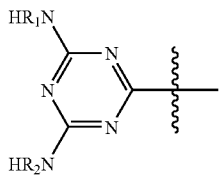

and said A comprises a pyrimidin-2,4,6-trion-3-yl moiety of a structural formula

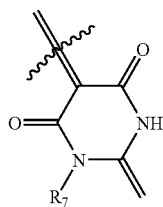

wherein $R_1$, $R_2$ and $R_7$ are H.

12. An intrinsically acentric electro-optic film comprising hydrogen-bonded chromophore compounds of the formula

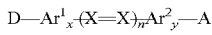

D—Ar$^1_x$—(X═X)$_n$Ar$^2_y$—A wherein D is a moiety comprising a plurality of hydrogen bond forming hydrogen donor groups; A is a moiety comprising a plurality of hydrogen bond-forming hydrogen acceptor groups; (—X═X—) is a π-bonded component comprising at least one of carbon and a heteroatom; n, x and y are independently $\geq 0$; and x+y is $\geq 1$.

13. The electro-optic film of claim 12 wherein said film is on a substrate comprising a component selected from a hydrogen-donor moiety and a hydrogen-acceptor moiety, for hydrogen bonding with said chromophore.

14. The electro-optic film of claim 13 wherein said substrate comprises the condensation product of hydroxylated indium tin oxide and an aminoalkyltrialkoxysilane.

15. The electro-optic film of claim 12 wherein said D comprises a moiety having a structural formula selected from

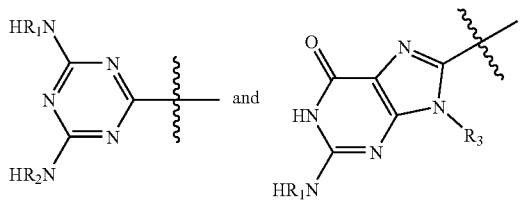

wherein $R_1$-$R_3$ are independently selected from hydrogen, electron-donating substituents and electron-withdrawing substituents.

16. The electro-optic film of claim 12 wherein said A comprises a moiety having a structural formula selected from

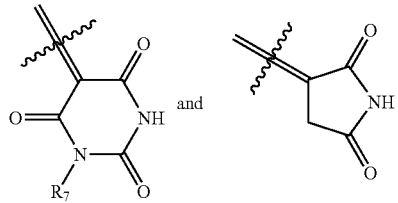

wherein $R_7$ is selected from hydrogen, electron-donating substituents and electron-withdrawing substituents.

17. The electro-optic film of claim 12 wherein (—X═X—)$_n$ comprises a moiety having a structural formula selected from (—C═C—)$_n$ and

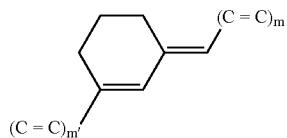

wherein m+m' $\geq 1$.

18. The electro-optic film of claim 12 wherein x+y=1.

* * * * *